(12) United States Patent
Schwab

(10) Patent No.: US 8,728,166 B2
(45) Date of Patent: May 20, 2014

(54) HYBRID INTERVERTEBRAL SPINAL FUSION IMPLANT

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 173 days.

(21) Appl. No.: 13/006,724

(22) Filed: Jan. 14, 2011

(65) Prior Publication Data

US 2011/0112643 A1 May 12, 2011

Related U.S. Application Data

(63) Continuation of application No. 11/527,122, filed on Sep. 26, 2006, now Pat. No. 7,875,075.

(60) Provisional application No. 60/720,555, filed on Sep. 26, 2005.

(51) Int. Cl.
*A61F 2/44* (2006.01)

(52) U.S. Cl.
USPC ............................................. 623/17.16

(58) Field of Classification Search
USPC .......................................... 623/17.11–17.16
See application file for complete search history.

(56) References Cited

U.S. PATENT DOCUMENTS

| | | | |
|---|---|---|---|
| 5,071,437 A | 12/1991 | Steffee | |
| 5,192,327 A | 3/1993 | Brantigan | |
| 5,397,364 A | 3/1995 | Kozak et al. | |
| 6,039,762 A | 3/2000 | McKay | |
| 6,126,688 A | 10/2000 | McDonnell | |
| 6,159,211 A | 12/2000 | Boriani et al. | |
| 6,241,733 B1 | 6/2001 | Nicholson et al. | |
| 6,296,665 B1 | 10/2001 | Strnad et al. | |
| 6,447,543 B1 | 9/2002 | Studer et al. | |
| 6,461,359 B1 | 10/2002 | Tribus et al. | |
| 6,626,943 B2 | 9/2003 | Eberlein et al. | |
| 6,645,248 B2 | 11/2003 | Casutt | |
| 6,679,887 B2 | 1/2004 | Nicholson et al. | |
| 6,712,852 B1 | 3/2004 | Chung et al. | |
| 6,716,245 B2 | 4/2004 | Pasquet et al. | |
| 6,790,233 B2 | 9/2004 | Brodke et al. | |
| 6,855,166 B2 | 2/2005 | Kohrs | |
| 6,899,735 B2 | 5/2005 | Coates et al. | |
| 6,979,353 B2 | 12/2005 | Bresina | |
| 6,997,953 B2 | 2/2006 | Chung et al. | |
| 7,044,972 B2 | 5/2006 | Mathys, Jr. et al. | |
| 7,137,997 B2 | 11/2006 | Paul | |

(Continued)

FOREIGN PATENT DOCUMENTS

| | | |
|---|---|---|
| WO | WO 00/16711 | 3/2000 |
| WO | WO 02/080823 | 10/2002 |

(Continued)

OTHER PUBLICATIONS

European Patent Office. Written Opinion of the International Searching Authority and Patent Cooperation Treaty International Search Report, International Application No. PCT/US2006/037781. Apr. 12, 2007.

*Primary Examiner* — Sameh Boles

(57) ABSTRACT

An implant made of at least two different materials. The implant may include materials with varying radiolucency and mechanical properties. Such a hybrid implant may offer controlled radiographic visibility and optimized structural properties for implant placement, including placement for use in spinal arthrodesis.

16 Claims, 7 Drawing Sheets

(56) References Cited

U.S. PATENT DOCUMENTS

| | | |
|---|---|---|
| 7,192,447 B2 | 3/2007 | Rhoda |
| 7,201,775 B2 | 4/2007 | Gorensek et al. |
| 7,232,463 B2 | 6/2007 | Falahee |
| 7,238,203 B2 | 7/2007 | Bagga et al. |
| 7,288,114 B2 | 10/2007 | Lange |
| 7,674,297 B2 | 3/2010 | Falahee |
| 7,806,932 B2 | 10/2010 | Webb et al. |
| 2003/0139812 A1 | 7/2003 | Garcia et al. |
| 2005/0049706 A1 | 3/2005 | Brodke et al. |
| 2005/0096745 A1 | 5/2005 | Andre et al. |
| 2005/0131539 A1* | 6/2005 | Kohrs ................ 623/17.11 |
| 2005/0177238 A1* | 8/2005 | Khandkar et al. ......... 623/17.11 |
| 2005/0187625 A1 | 8/2005 | Wolek et al. |

FOREIGN PATENT DOCUMENTS

| | | |
|---|---|---|
| WO | WO 03/068111 | 8/2003 |
| WO | WO 2004/071346 | 8/2004 |
| WO | WO 2007/035968 | 3/2007 |

* cited by examiner

HYBRID INTERVERTEBRAL SPINAL FUSION IMPLANT

CROSS REFERENCE

The present application is a continuation of and claims priority from U.S. Utility patent application Ser. No. 11/527,122, filed on Sep. 26, 2006, now U.S. Pat. No. 7,875,075, which claims priority from U.S. Provisional Patent Application Ser. No. 60/720,555, filed on Sept. 26, 2005, entitled "Hybrid Intervertebral Spinal Fusion Implant." The following applications also claim priority to the above referenced provisional application and are related to the present application. They are incorporated by reference herein:

U.S. Utility patent application Ser. No. 11/527,121 filed on Sept. 26,2006 and entitled "Transforaminal Hybrid Implant;" and U.S. Utility patent application Ser. No. 11/527,123 filed on Sept. 26,2006 and entitled "Anterior Hybrid Implant."

TECHNICAL FIELD

The present invention relates generally to the field of medical implants and methods, and more specifically to interbody spinal implants which may be adapted for placement into an implantation space created across the height of a disc space between two adjacent vertebral bodies for the purpose of correcting disease, dysfunction, or degeneration at that interspace, and any related methods. The spinal implants may be made of a plurality of implant materials which bear differing degrees of radiographic lucency. These materials may include bone and may or may not be resorbable. The implants of some embodiments are adapted such that radiographic visualization of operative placement and eventual bone healing can be observed.

BACKGROUND

Implants for placement in the intervertebral space between adjacent vertebral bodies in the spine come in a wide range of shapes and sizes. These implants are usually made entirely of one material, although the type of material can vary significantly between specific implants. Such implants for use in human spinal surgery include implants made entirely of metals, such as titanium or stainless steel, or synthetic radiolucent materials such as carbon-carbon composites or poly-ether-ether-ketone (PEEK). Implants may have a structure designed to promote fusion across adjacent vertebral bodies by allowing bone to grow through and around the implant. The operative placement of intervertebral implants is optimized by radiographic opacity. However, a relatively radiolucent implant material optimizes postoperative evaluation of bone growth and fusion across an intervertebral space. While these implants may contain marking beads or radio opaque markers they do not structurally benefit from radio opaque materials. In some configurations, metals, some of which are opaque on radiographs, provide greater strength and resistance to impaction during implantation. Metallic implants may offer reduced wall thickness of structural components and offer increased volume for bone graft and other agents within an implant.

As it is desirable to take advantage of benefits of radiolucent and radio-opaque materials in an implant, there exists a need for an improved implant made of different structural materials with different properties of radiographic appearance. For some implants, it is desirable to provide optimization of mechanical properties, while permitting generous bone filling and bone through-growth. These characteristics may be applied in some embodiments in combination with an ability to radiographically determine bone-implant interaction and bone growth into and around the implant.

SUMMARY

Embodiments of the invention may include an artificial interbody spinal fusion implant made of structural materials with varying radiolucency and mechanical characteristics. Implants may be provided for insertion at least in part into an implantation space formed across the height of a disc space between adjacent vertebral bodies of a human spine. The implant of some embodiments consists of at least two radiographically distinct imaging materials: a radiolucent portion, and a radio-opaque portion. The radio-opaque materials of some embodiments are arranged toward the vertebral endplates with minimal obstruction to radiographic visualization through the implant from anterior to posterior and/or from lateral directions. Embodiments of the implant may include upper and lower portions adapted to be placed within the intervertebral space to contact and support the adjacent vertebral bodies. Upper and lower portions of the implant may include at least one opening in communication with one another and adapted to hold bone growth promoting material and/or bone graft for permitting the growth of bone from vertebral body to vertebral body through the implant. Embodiments of the invention include an artificial interbody spinal implant containing at least two different materials for insertion at least in part into an implantation space formed across the height of a disc space between adjacent vertebral bodies of a spine. Implant embodiments may employ materials that bear a structural role in the design of the implant, and at least a portion of a leading end of the implant may have a reduced height to facilitate insertion of said implant between the two adjacent vertebral bodies. Implants may have a maximum length less than and approximating the posterior to anterior or right to left length of the vertebral bodies. Some embodiments also include a bone engaging surface formed on the exterior of at least the upper and lower portions for engaging the adjacent vertebral bodies, such as one or more protrusions, ratchets, spikes, roughened surfaces or knurling. Embodiments of the implant may be combined with a bone growth or bone healing promoting material such as, but not limited to, bone, bone derived products, demineralized bone matrix, mineralizing proteins, ossifying proteins, bone forming cell differentiating substance, bone morphogenetic protein, hydroxyapatite, and gene therapy material leading to the production of bone. Embodiments of the implant may also be combined with a therapeutic substance for the treatment of infection, tumor or other pathologic process. In some embodiments of the invention, one component material is relatively, or absolutely radiolucent. In some embodiments of the invention, one component material is radio-opaque. One component material of the implant may be at least in part resorbable. In some embodiments, at least a portion of an implant is treated to promote bone in-growth between the implant and adjacent vertebral bodies. Embodiments of the implant may be used in combination with at least one spinal fixation implant. Embodiments of the implant may include a hollow interior and at least one area for attachment or interaction with an insertion device for surgical placement or removal from the intervertebral space. Upper and lower surfaces of some embodiments of the implant may include a plurality of openings. Embodiments of the implant may be designed to be inserted adjacent to a second implant into a disc space between adjacent vertebral bodies, the second implant being of identical or differing shape. At least one opening may be between the leading and trailing ends of embodiments of the implant. Upper and lower portions or surfaces of embodiments of the implant may be at least in part generally parallel to one another or may be configured with an angular relationship to each other for allowing angulation of adjacent vertebral bodies relative to each other.

Another embodiment of the invention is an intervertebral implant for promoting fusion between adjacent vertebral bodies. The implant may include a first body made at least in part of a first material, the first body having an inferior laterally extending member, a support coupled to and extending superiorly away from the inferior laterally extending member, and a superior laterally extending member coupled to the support. The implant may also include a second body made at least in part of a second material, the second body configured to fit at least partially between the inferior laterally extending member and the superior laterally extending member.

Yet another embodiment of the invention is an intervertebral implant for promoting fusion between two adjacent vertebral bodies. The implant may include first and second radio-opaque plates for engaging with opposing endplates of the adjacent vertebral bodies, the first and second plates being constructed to form a space therebetween, and first and second radiolucent blocks placed between the first and second plates at opposite lateral sides of the space. An interior void may be formed in the space between the first and second plates, the interior void being partially enclosed on at least two sides by the first and second radiolucent blocks.

Still another embodiment of the invention is an intervertebral implant with a lateral dimension, an anterior to posterior dimension, and an inferior to superior vertical dimension, the implant for placement between adjacent vertebral bodies. The implant may include an inferior laterally extending member, a superior laterally extending member, and a substantially radiolucent body configured to fit at least partially between the inferior laterally extending member and the superior laterally extending member. Two or more supports coupled to and extending between the inferior laterally extending member and the superior laterally extending member may also be included, and a relative alignment among the two or more supports, as viewed radiographically from at least one of anterior, posterior, and lateral sides, indicates a rotational position of the implant about a vertical axis.

DETAILED DESCRIPTION

The following description is intended to be representative only and not limiting and many variations can be anticipated according to these teachings, which are included within the scope of this inventive teaching. Reference will now be made in detail to embodiments of this invention, examples of which are illustrated in the accompanying drawings. Wherever possible, the same reference numbers will be used throughout the drawings to refer to the same or like parts.

Figure 1:
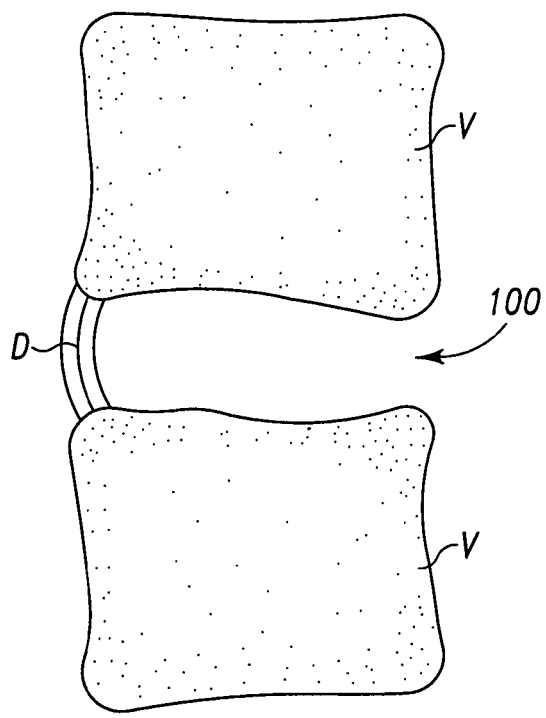
FIG. 1 is a side view of two adjacent vertebral bodies in a lumbar spine with an implantation space formed across the height of the spinal disc space.
Figure 2:
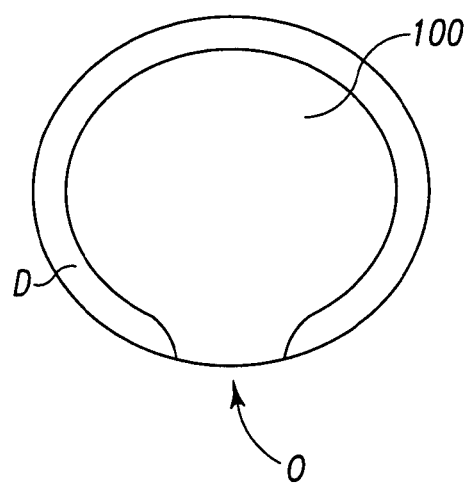
FIG. 2 is a top plan view of a vertebral body in a lumbar spine with an implantation space formed through a posterior approach.
Figure 3:
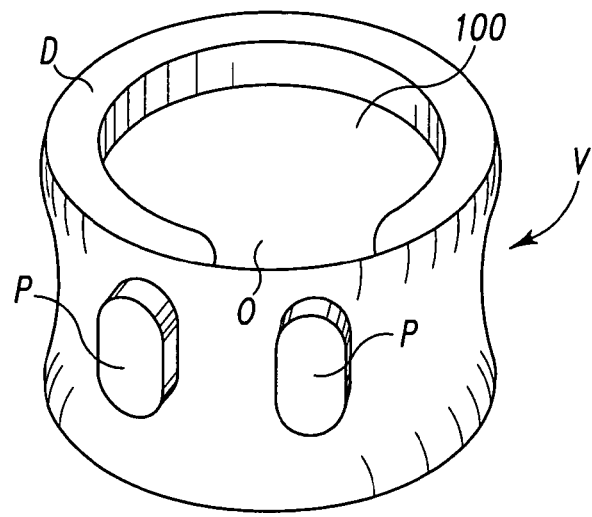
FIG. 3 is a side perspective view of the implantation space of FIG. 2.

FIGS. 1-3 show an implantation space 100 formed across the height of a spinal disc D between vertebral bodies V in the lumbar spine. In other embodiments, the vertebral bodies may be bodies of the cervical or thoracic spine as well. It is understood that numerous methods exist and that any method and instrumentation designed for the purpose may be applied to prepare the desired implantation space and perform disc and soft tissue removal in such a manner as to be adapted to receive the implants of the present invention. It is also understood that implantation space preparation commonly leaves residual disc material D prior to implant placement.

FIG. 3 shows the implantation space 100, which has been prepared by partial disc and soft tissue removal adjacent to the vertebral body V. The preparation in FIG. 3 is shown as a posterior lumbar surgical approach, and the opening O into the disc space from the posterior is shown. The opening O may also be an opening prepared for transforaminal or oblique surgical approaches. Residual portions P of the vertebral pedicles are also shown.

Figure 4:
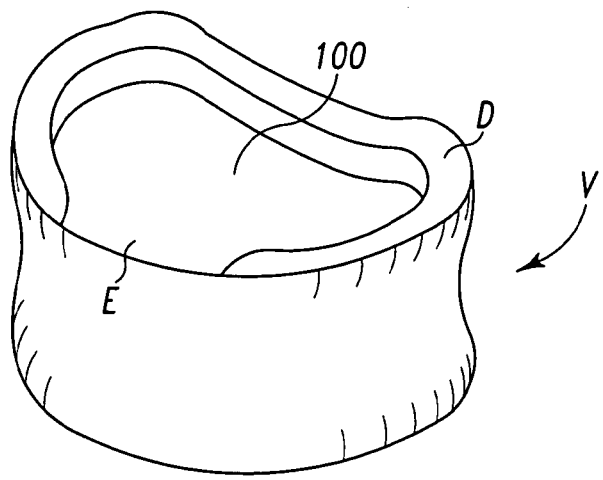
FIG. 4 is a perspective view of an implantation space formed through an anterior approach.

FIG. 4 shows the implantation space 100, which has been prepared by partial disc and soft tissue removal adjacent to the vertebral body V. The preparation in FIG. 4 is shown as an anterior surgical approach and the entrance E into the disc space from the anterior is shown. This representation can reflect a cervical, thoracic, or lumbar spinal intervertebral space preparation.

Figure 5:
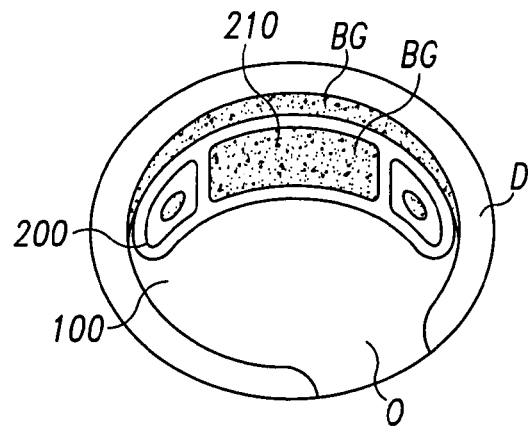
FIG. 5 is a top plan view of a vertebral body in the lumbar spine with an embodiment of an implant positioned in the implantation space of FIG. 2.

FIG. 5 shows a unilateral implant 200 seated in the implantation space 100 in accordance with an embodiment of the present invention. Bone graft material BG is shown anterior to the unilateral implant 200, as well as within a central void 210 of the unilateral implant 200.

Figure 6:
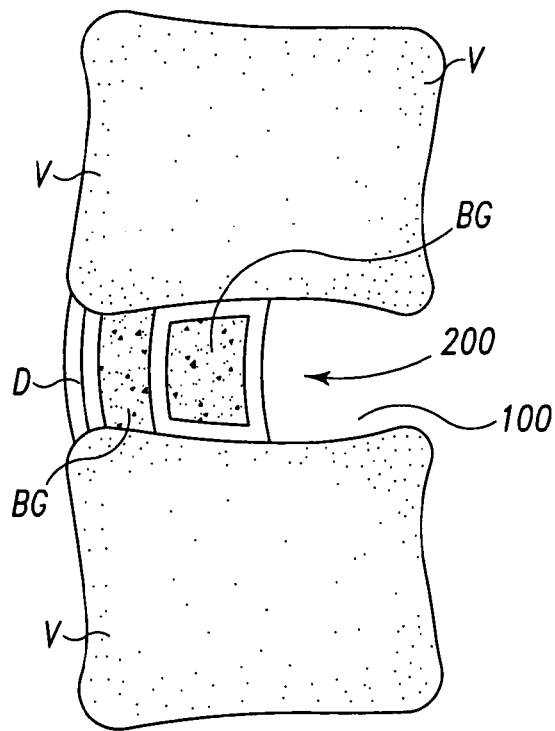
FIG. 6 is a side view of two adjacent vertebral bodies with the implant of FIG. 5 positioned in the implantation space of FIG. 2 through a posterior approach.

FIG. 6 shows a unilateral implant 200 seated in the implantation space 100. Bone graft material BG is shown anterior to the unilateral implant 200 but posterior to remaining disc D, as well as within the central void 210 of the unilateral implant 200.

Figure 7:
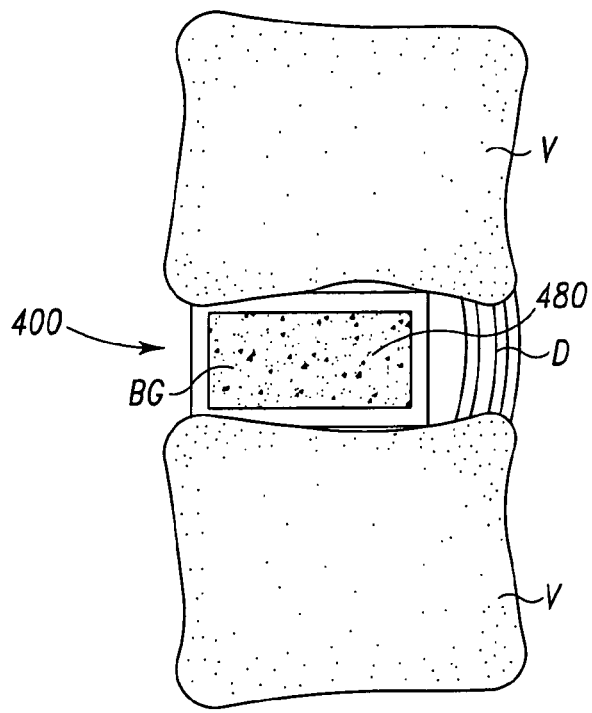
FIG. 7 is a side view of two adjacent vertebral bodies with an implant positioned in the implantation space of FIG. 2 through an anterior approach.

FIG. 7 shows an anterior implant 400 seated in the implantation space 100. Bone graft material BG is shown within a cavity 480 of the anterior implant 400.

Figure 8:
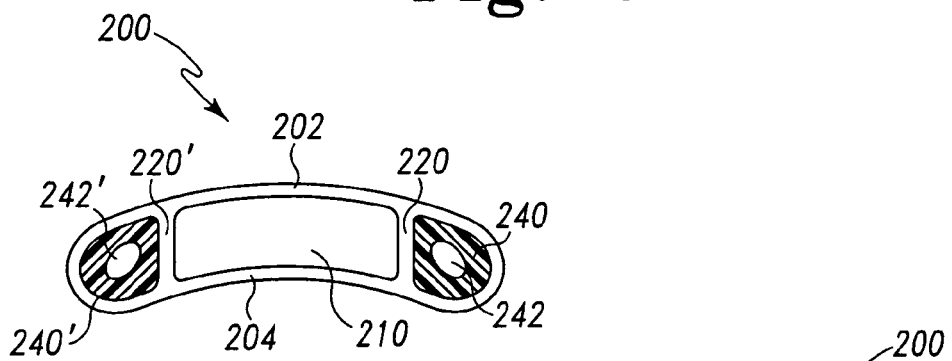
FIG. 8 is a top plan view of the implant of FIG. 5

FIG. 8 shows the unilateral implant 200 with an anterior aspect 202 and a posterior aspect 204. The central void 210 is shown. Traversing support structures 220, 220' extend from anterior 202 to posterior 204 aspects of the implant. In the lateral aspects of the unilateral implant 200 radiolucent blocks 240, 240' are shown, each with a central cavity 242, 242'.

Figure 9:
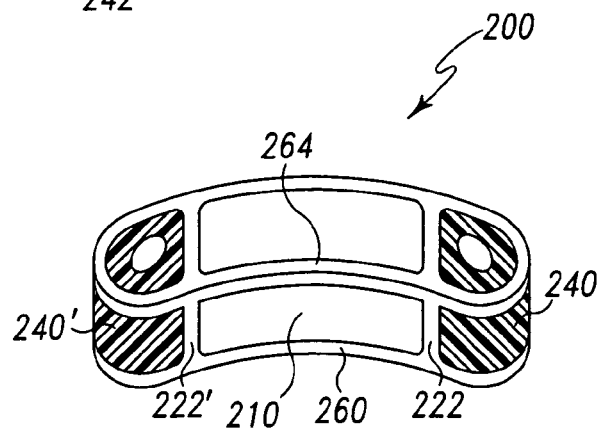
FIG. 9 is a rear perspective view of the implant of FIG. 5.

FIG. 9 shows the unilateral implant 200 as described in FIG. 8. The view from a posterior perspective shows the central void 210, the radiolucent blocks 240, 240' and posterior support columns 222, 222' which extend from an inferior aspect 260 to a superior aspect 264 of the implant.

Figure 10:
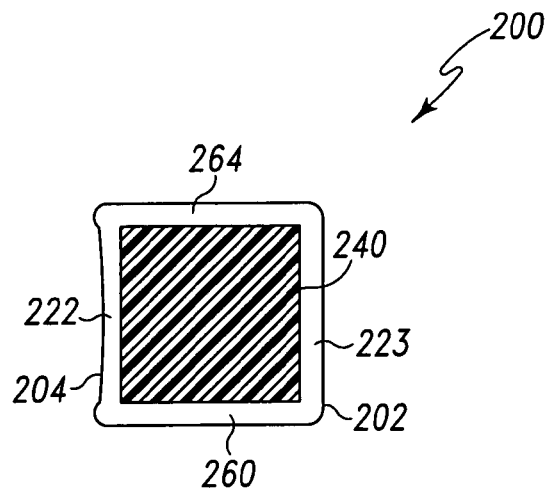
FIG. 10 is a side view of the implant of FIG. 5.

FIG. 10 shows the unilateral implant 200 as described in FIG. 8 from a lateral view. The radiolucent block 240 is shown positioned between the superior aspect 264 and the inferior aspect 260 of the implant. A posterior support column 222 and an anterior support column 223 between the superior aspect 264 and inferior aspect 260 are shown. In a lateral projection, anterior 202 and posterior 204 aspects to the implant are noted.

Figure 11:
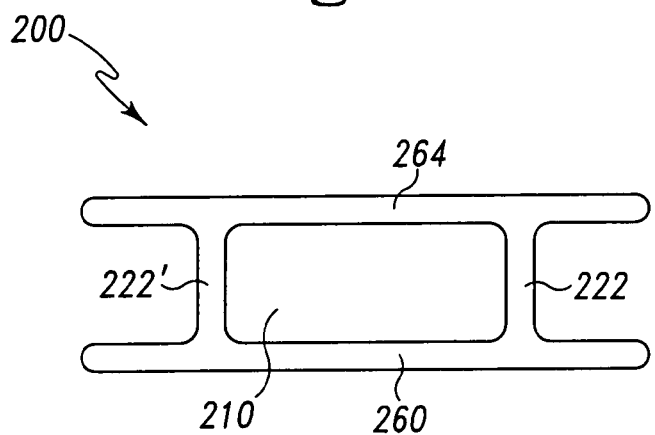
FIG. 11 is a rear view of the implant of FIG. 5.

FIG. 11 shows a posterior view of the implant as described in FIGS. 8 and 9 without appearance of the radiolucent blocks 240, 240', in order to show radiographic appearance. Only the posterior support columns 222, 222' extending between the inferior aspect 260 and the superior aspect 264 of the implant are visualized radiographically due to the selected radio-opaque nature of the material implemented in this embodiment. Anterior support columns 223, 223' are hidden behind posterior support columns 222, 222' when the unilateral implant 200 is visualized radiographically directly from the posterior.

Figure 12:
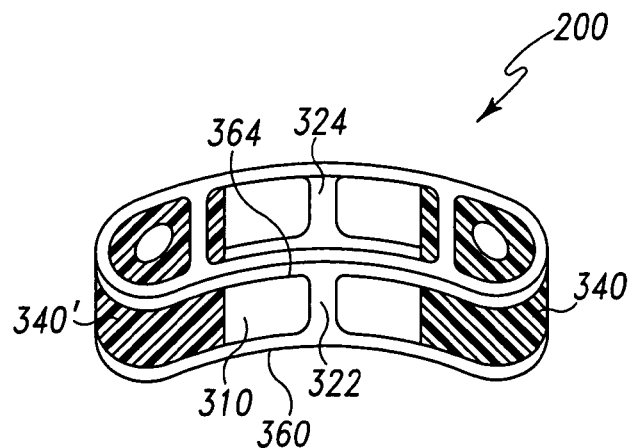
FIG. 12 is a rear perspective view of another embodiment of an implant for use in the implantation space of FIG. 2.

FIG. 12 shows another embodiment of the invention with a center-support implant 300 in rear perspective view. A central volume 310, and radiolucent lateral blocks 340, 340', as well as anterior support structure 324, and posterior support structure 322 are noted.

Figure 13:
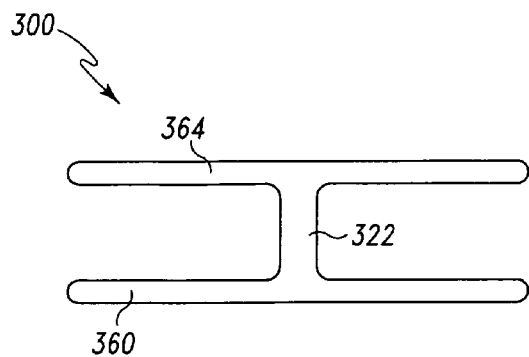
FIG. 13 is a rear view of the implant of FIG. 12.

FIG. 13 shows a posterior view of the implant as described in FIG. 12 without appearance of the radiolucent lateral blocks 340, 340' in order to show radiographic appearance. Only the posterior support structure 322, which overlaps in this view the anterior support structure 324, seen in FIG. 12, is visualized radiographically between the inferior portion 360 and the superior portion 364 of the implant due to the selected radio-opaque nature of the material implemented in this embodiment.

Figure 14:
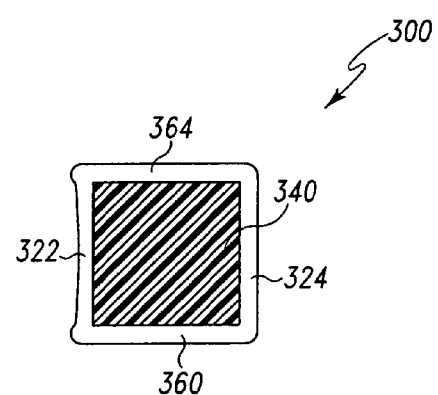
FIG. 14 is a side view of the implant of FIG. 12.

FIG. 14 shows the center-support implant 300 as described in FIG. 12 from a lateral view. The radiolucent lateral block 340 is shown positioned between the superior portion 364 and the inferior portion 360 of the implant. In this lateral projection the anterior support structure 324 and posterior support structure 322 of the implant are noted.

Figure 15:
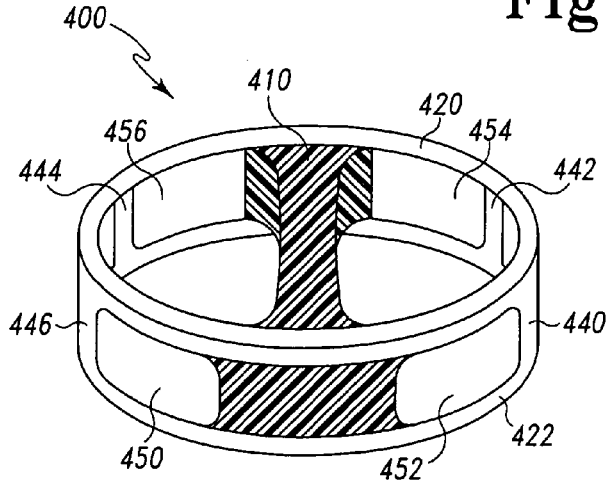
FIG. 15 is a rear perspective view an embodiment of an implant suited for anterior placement into a cervical or lumbar intervertebral disc space.

FIG. 15 illustrates an anterior implant 400. In some embodiments, the anterior implant 400 may be placed through an anterior surgical approach. However, the anterior implant 400 may also be placed by other surgical approaches such as, but not limited to, an anterior-oblique approach or a lateral approach. A large central strut 410 made of radiolucent material is shown traversing the implant. Upper rim 420 and lower rim 422 are attached to the central strut 410 and further supported and connected to one another through supportive structures 440, 442, 444, 446. Openings through the sides of the implant are noted 450, 452, 454, 456. These openings may permit for the growth of bone through and into anterior implant 400, though the invention is not so limited.

Figure 16:
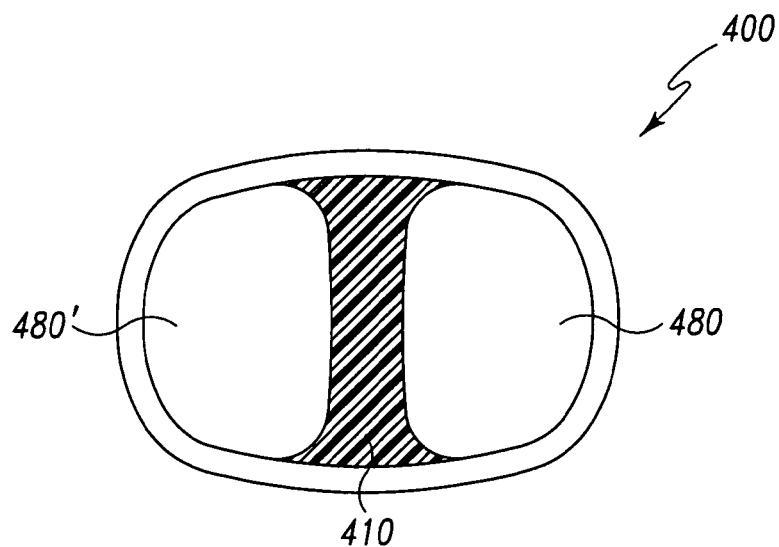
FIG. 16 is a top plan view of the implant of FIG. 15.

FIG. 16 shows a top plan view of the anterior implant 400 as described in FIG. 15. The large central strut 410 is noted. Two cavities 480, 480' within the anterior implant 400 are shown on either side of the strut 410. These cavities may permit for the growth of bone through and into anterior implant 400, though the invention is not so limited.

Figure 17:
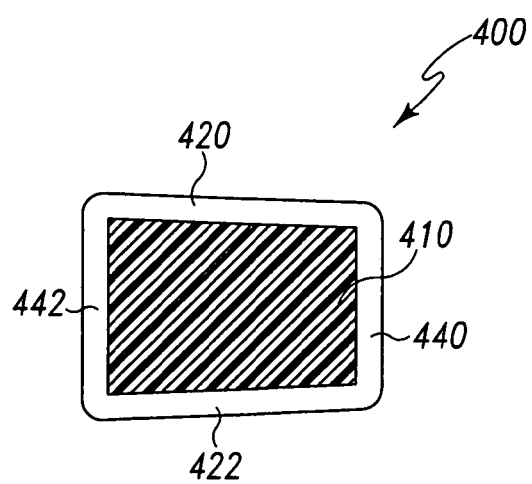
FIG. 17 is a side view of the implant of FIG. 15.

FIG. 17 shows a lateral view of the anterior implant 400 as described in FIGS. 15 and 16. Upper rim 420 and lower rim 422 are shown, as is the lateral view of the central strut 410. Given the radiolucent nature of the central strut 410, on radiographic visualization only the upper rim 420 and lower rim 422 as well as radio-opaque supportive structures 440, 442 would be noted. The remaining two supportive structures 444, 446 noted in FIG. 15 are obscured in a lateral view by the supportive structures 440, 442. Further, angulation between the upper rim 420 and lower rim 422 may facilitate insertion of anterior implant 400 between the two adjacent vertebral bodies and permit control of sagittal plane intervertebral alignment.

While the implants are intended primarily for use in spinal fusion, it is appreciated that they may be modified or adapted to receive fusion promoting substances and/or materials within them such as, but not limited to cancellous bone, bone derived products, chemotherapeutic agents, antimicrobial agents, or others. In some embodiments, the implants consists of materials such as, but not limited to, titanium and its alloys, ASTM material, cobalt chrome, tantalum, ceramic, polyether-ether-ketone (PEEK), various plastics, plastic composites, carbon fiber composites, coral, and can include artificial materials which are at least in part bioresorbable. The radiographic appearance of the structural materials employed in the implants are intended to be of varying nature such that optimal visualization of implant placement, implant-bone interfaces and/or bone ingrowth and through-growth can be achieved.

While the descriptions reveal various relationships, parallel or not, of upper to lower surfaces of the implants, it should be noted that deliberate angulation between surfaces relative to each other is possible. Subsequently, when implanted into the spine, such implants permit position of the adjacent vertebral bodies in angular relationship to each other to restore the natural curvature of the spine, such as lordosis for example. It should also be noted that significant variations in shape of the implants are possible including but not limited to: kidney shaped, rounded, wedge shaped, cylindrical, trapezoidal, rectangular, oblong, and oval.

Outer surfaces may contain threading or particular unevenness for improved insertion or anchorage into surrounding tissues or bone. In any of the embodiments of the present invention, the implants may include, be made of, treated, coated, filled, used in combination with, or have a hollow space or opening for containing artificial or naturally occurring materials and/or substances suitable for implantation in the human spine. These materials, and/or substances, may include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone, antibiotics, cancer treating substances, infection treating substances or other disease treating substances. The implant can include, at least in part materials that are bioabsorbable and/or resorbable in the body. The implants of the present invention can be formed of a porous material or can be formed of a material that intrinsically participates in the growth of bone between adjacent vertebral. At least a portion of the implant may be treated to promote bone ingrowth between the implant and the adjacent vertebral bodies.

The implant of the present invention may be used in combination with a spinal fixation device such as any device, regardless of material, that can be inserted into any portion of the spine, such as but not limited to interbody spinal implants, structural bone grafts, mesh, cages, spacers, staples, bone screws, plates, rods, tethers of synthetic material or wires, or other spinal fixation instrumentation. While the invention has been described with reference to particular embodiments, it will be appreciated by those of ordinary skill in the art that various modifications can be made to the invention itself without departing from the spirit and scope thereof. All changes and modifications that are within the spirit of the invention are hereby anticipated and claimed.

What is claimed is:

1. An intervertebral implant for promoting fusion between adjacent vertebral bodies, comprising:
    an inferior laterally extending member having a first anterior aspect and a first posterior aspect separated at least in part by a central void and joined together by respective end members;
    a superior laterally extending member having a second anterior aspect and a second posterior aspect separated at least in part by the central void and joined together by respective end members;
    wherein said inferior and superior laterally extending members comprise a biocompatible metal having an outer surface with substantial unevenness for promoting bone growth thereon; and
    a body made at least in part of a biocompatible polymer, the body being positioned between said inferior laterally extending member and said superior laterally extending member,
    wherein said central void extends through an upper surface of said inferior laterally extending member and a lower surface of said superior laterally extending member and through opposite first side portions of said implant between said upper and lower surfaces, said central void being at least partially enclosed between opposite second side portions of said implant that extend between said first side portions by said body, and wherein said body is positioned so as to avoid blocking portions of said central void that extend through said first side portions.

2. The intervertebral implant of claim 1, wherein said biocompatible metal is radiographically detectable.

3. The intervertebral implant of claim 1, wherein the biocompatible metal is titanium.

4. The intervertebral implant of claim 1, wherein said inferior laterally extending member comprises a plate of titanium disposed on an inferior surface of said body, said layer of titanium having a roughened surface configured to contact an inferior vertebral body.

5. The intervertebral implant of claim 1, wherein said superior laterally extending member comprises a plate of titanium disposed on a superior surface of said body, said layer of titanium having a roughened surface configured to contact a superior vertebral body.

6. The intervertebral implant of claim 1, wherein said biocompatible polymer is PEEK.

7. The intervertebral implant of claim 1, wherein said biocompatible polymer is radiographically detectable.

8. The intervertebral implant of claim 1, wherein said biocompatible polymer is radiolucent.

9. The intervertebral implant of claim 1, wherein said biocompatible polymer is less radiographically detectable than said biocompatible metal.

10. The intervertebral implant of claim 1, wherein said implant is configured to be positioned in a disc space between adjacent vertebrae, the implant further comprising a second implant configured to be inserted adjacent the implant in the disc space.

11. The intervertebral implant of claim 1, wherein said biocompatible polymer comprises PEEK and said biocompatible metal comprises a coating of titanium on top and bottom surfaces of said inferior and superior laterally extending members.

12. An intervertebral implant for promoting fusion between two adjacent vertebral bodies comprising:
    first and second opposing radio-opaque plates, said first plate having a lower surface for engaging a first endplate of said adjacent vertebral bodies and said second plate having an upper surface for engaging a second endplate of said second adjacent vertebral bodies; and
    a radiolucent block disposed between said first and second plates;
    wherein an interior void is formed in the space between said first and second plates, the interior void extending through the upper and lower surfaces and through opposite first side portions of the implant that extend between the upper and lower surfaces, the interior void being at least partially enclosed between opposite second side portions of said implant that extend between said first side portions by said radiolucent block, wherein said radiolucent block is positioned so as to avoid blocking portions of said interior void that extend through said first side portions, and wherein said interior void permits for the growth of bone through and into said radiolucent block.

13. The intervertebral implant of claim 12, wherein said upper and lower surfaces of said first and second opposing radio-opaque plates comprise a biocompatible metal having an outer surface with substantial unevenness for promoting bone growth thereon.

14. The intervertebral implant of claim 12, wherein said first and second radio-opaque plates are at least in part made from titanium.

15. The intervertebral implant of claim 12, wherein said radiolucent block is at least in part made from PEEK.

16. The intervertebral implant of claim 12, wherein said radiolucent block comprises PEEK and said upper and lower surfaces are each planar and include a coating of titanium.

* * * * *